United States Patent
Stanley et al.

(10) Patent No.: US 11,172,751 B2
(45) Date of Patent: Nov. 16, 2021

(54) METHOD OF DEFINING A TREATMENT AREA OF AN APPLICATOR FOR REGISTRATION WITH A CONDITION TO BE TREATED

(71) Applicant: The Procter & Gamble Company, Cincinnati, OH (US)

(72) Inventors: Scott Kendyl Stanley, Mason, OH (US); Andrew Paul Rapach, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 108 days.

(21) Appl. No.: 16/687,771

(22) Filed: Nov. 19, 2019

(65) Prior Publication Data
US 2020/0196736 A1    Jun. 25, 2020

Related U.S. Application Data

(60) Provisional application No. 62/781,848, filed on Dec. 19, 2018.

(51) Int. Cl.
*A45D 44/00* (2006.01)
*A61M 35/00* (2006.01)
(Continued)

(52) U.S. Cl.
CPC ........... *A45D 44/002* (2013.01); *A61M 35/10* (2019.05); *G06K 9/00234* (2013.01); *G06K 9/00281* (2013.01); *G06T 7/0016* (2013.01); *G06T 7/40* (2013.01); *G06T 7/60* (2013.01); *A45D 2044/007* (2013.01); *A61M 2210/04* (2013.01);
(Continued)

(58) Field of Classification Search
None
See application file for complete search history.

(56) References Cited

U.S. PATENT DOCUMENTS

| | | | |
|---|---|---|---|
| 9,996,981 B1 * | 6/2018 | Tran | G06K 9/4671 |
| 2003/0223622 A1 * | 12/2003 | Simon | G06K 9/00281 |
| | | | 382/118 |

(Continued)

FOREIGN PATENT DOCUMENTS

WO    9955394 A1    11/1999

OTHER PUBLICATIONS

International Search Report and Written Opinion; Application Ser. No. PCT/US2019/067028, dated Apr. 8, 2020, 16 pages.

*Primary Examiner* — Soo Shin
(74) *Attorney, Agent, or Firm* — Amanda T Barry

(57) ABSTRACT

Method of defining at least one treatment area including receiving a first set of data from a digital geometric representation of a target area; receiving a second set of data representing at least a portion of an applicator designed to contact the target area; digitally overlying the second set of data over the first set of data to generate a first digital overlay; digitally defining a treatment area on the first digital overlay surrounding the condition; generating a third set of data representing a portion of the applicator and the treatment area; digitally overlying the third set of data over the first set of data to generate a second digital overlay representing coverage of a condition by the treatment area; and generating a first electronic image that includes a visual depiction of the second digital overlay.

8 Claims, 6 Drawing Sheets

(51) Int. Cl.
    *G06K 9/00*     (2006.01)
    *G06T 7/00*     (2017.01)
    *G06T 7/40*     (2017.01)
    *G06T 7/60*     (2017.01)
    *G16H 20/10*     (2018.01)
    *G16H 30/40*     (2018.01)

(52) U.S. Cl.
    CPC ........ *A61M 2210/0606* (2013.01); *G06T 2207/30088* (2013.01)

(56) References Cited

U.S. PATENT DOCUMENTS

| | | | |
|---|---|---|---|
| 2006/0023228 A1* | 2/2006 | Geng | A61B 5/411 356/601 |
| 2009/0280150 A1* | 11/2009 | Kamen | A45D 44/002 424/401 |
| 2010/0191314 A1* | 7/2010 | Young | A61F 7/0241 607/109 |
| 2012/0192884 A1* | 8/2012 | Nasu | A45F 3/18 132/200 |
| 2017/0008566 A1 | 1/2017 | Willerton | |
| 2017/0061609 A1* | 3/2017 | Son | G06Q 30/0641 |
| 2017/0354805 A1 | 12/2017 | Stanley et al. | |
| 2017/0354806 A1 | 12/2017 | Stanley et al. | |
| 2018/0206616 A1* | 7/2018 | Alary | A45D 40/30 |
| 2020/0046226 A1* | 2/2020 | Stanley | A61B 5/0064 |
| 2020/0196736 A1* | 6/2020 | Stanley | G06T 7/60 |
| 2020/0197677 A1 | 6/2020 | Stanley et al. | |

\* cited by examiner

METHOD OF DEFINING A TREATMENT AREA OF AN APPLICATOR FOR REGISTRATION WITH A CONDITION TO BE TREATED

FIELD OF THE DISCLOSURE

The disclosure relates to methods for registering an active agent and/or defining a treatment area on an applicator containing an active agent with a condition in a target area to which the applicator is applied.

BACKGROUND

Agents for affecting target structures are well known. Temperature affects may be induced by the application of hot or cold agents to the target. The appearance of a target may be affected by cosmetic and decorative agents. Electric current, voltages, and electric and magnetic fields may be applied to a target using local applicators. For biological targets, surface properties may be impacted by the use of topical application of moisturizers, medicaments and other treatment actives.

The effectiveness of the active agent may be impacted by the nature of the applicator available to facilitate the interaction of the active agent with the target structure. Typical applicators are less than precise with respect to their conformance to the target structure and the use of one-size, or a few sizes, fits all tends to compromise the actual performance of the active agent. Such applicators can, for example, resulting in the active agent not being applied effectively to a target area and/or require active agents to be spread over larger areas of the applicator than the size of the area having the condition to be treated due to misalignment of the applicator when applied.

SUMMARY

A method of defining at least one treatment area of an applicator containing an active agent for treating at least one condition on a target area is disclosed. The method can include receiving on a processor a first set of data representing the target area and at least one condition disposed on the target area to be treated by the active agent. The first set of data being received from a digital representation (geometric and or color/texture) of the target area stored on a memory or streamed in real time; receiving on a processor a second set of data representing at least a portion of an applicator designed to contact the target area; digitally overlying the second set of data over the first set of data to generate a first digital overlay; digitally defining at least one treatment area on the first digital overlay surrounding the at least one condition; generating a third set of data representing the at least the portion of the applicator and the at least one treatment area; digitally overlying the third set of data over the first set of data to generate a second digital overlay representing coverage of at least one condition by the at least one treatment area; and generating a first electronic image that includes a visual depiction of the second digital overlay.

Also disclosed is a method of defining at least one treatment area of an applicator containing an active agent for treating at least one condition on a target area can include receiving on a processor a first set of data representing the target area and at least one condition disposed on the target area to be treated by the active agent. The first set of data being received from a digital geometric representation of the target area stored on a memory or streamed in real time; receiving on a processor a second set of data representing at least a portion of an applicator designed to contact the target area; digitally overlying the second set of data over the first set of data to generate a first digital overlay; digitally defining at least one treatment area on the first digital overlay surrounding the at least one condition; generating a third set of data representing the at least the portion of the applicator and the at least one treatment area; digitally overlying the third set of data over the first set of data to generate a second digital overlay representing substantially complete alignment of the applicator on the target surface and illustrating coverage of the at least one condition by at least one treatment area; digitally overlaying the third set of data over the first set of data to generate a third digital overlay representing at least partial misalignment of the applicator on the target surface and illustrating coverage of the at least one condition by the at least one treatment area; adjusting one or more of the size and or location of the at least one treatment area if at least one treatment area does not cover all of the at least one condition in the second digital overlay; and/or the at least one treatment area does not cover all of the at least one condition in the third digital overlay and generating a fourth set of data representing the at least the portion of the applicator and the adjusted at least one treatment area; digitally overlaying the fourth set of data over the first set of data to generate a fourth digital overlay; and generating one or more of: a first electronic image that includes a visual depiction of the second digital overlay; a second electronic image that includes a visual depiction of the third digital overlay; and a third electronic image that includes a visual depiction of the fourth digital overlay.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Figure 1:
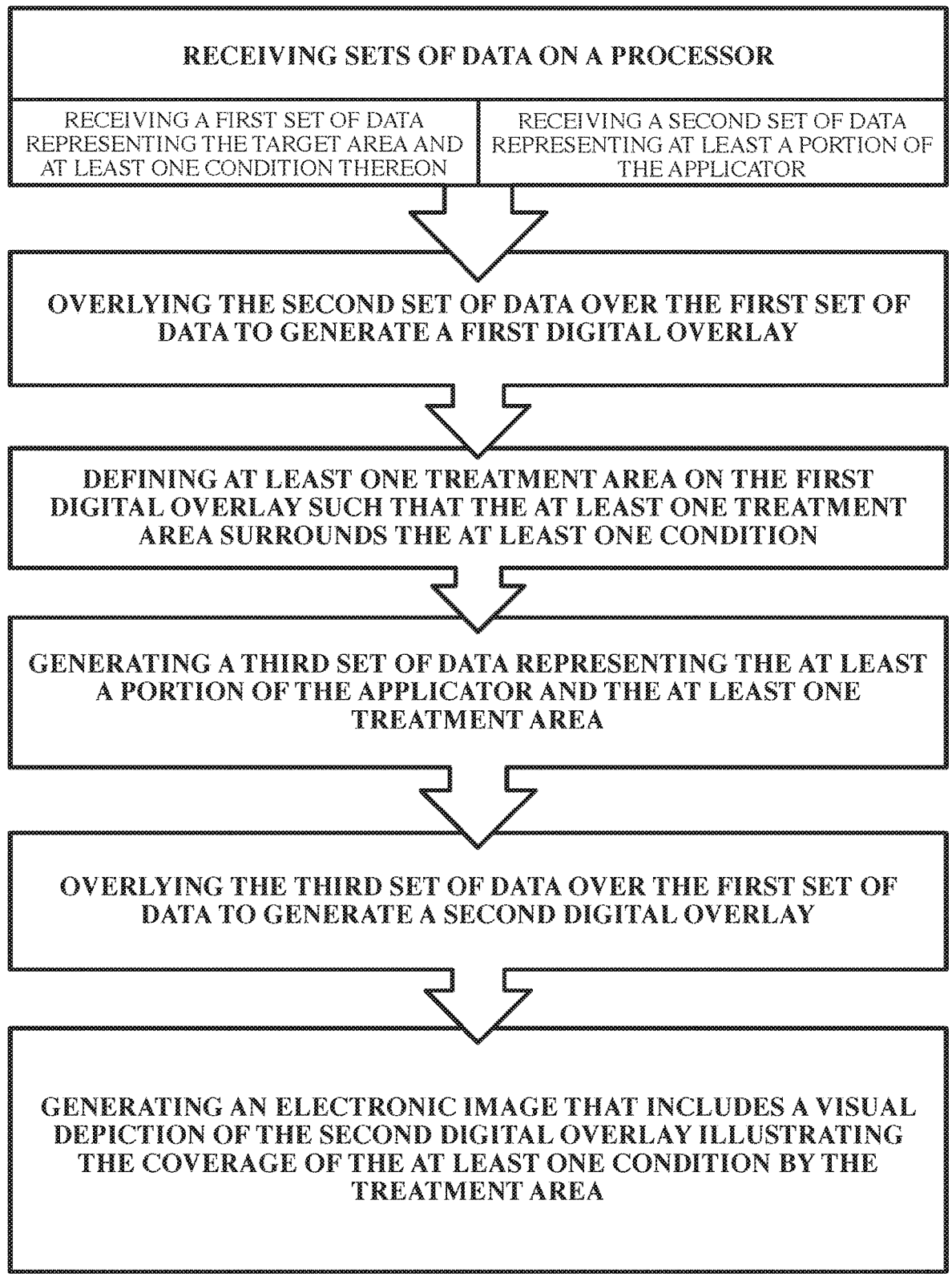
FIG. 1 is a process diagram illustrating a method in accordance with embodiments of the disclosure.

The method can include determining a location and/or registration of a treatment area 12 of an applicator 10 having an active agent with a condition 13 present on a target area 11 to be treated with the active agent. In embodiments, a method can include defining a treatment area 12 on an applicator 10 having a location and size corresponding to a location and size of a condition 13 present on a target area 11 to be treated with an active agent applied to the applicator 10 in the treatment area 12. The method can include defining the treatment area 12 to accommodate for potential misalignment of the applicator 10 when applied to the target area 11 to ensure that the condition 13 is contacted with the active agent present in the treatment area. The method can include creating an applicator 10 having a treatment area 12 registered with a condition 13 present on a target area 11 to be treated with the active agent. Throughout the disclosure, the term "active agent" will be used and should be understood to include therapeutic, cosmetic, medicinal, and other actives for treating or applying to a condition.

Methods in accordance with embodiments can beneficially allow targeted location of a treatment area 12 to provide efficient contact by an active agent of a condition 13 in a treatment area. This can allow active agents to be more localized in treating a condition 13 and/or allow multiple active agents to be utilized on a single applicator 10 for treating different conditions 13 on the target area 11 with localized treatment of each condition. In embodiments, the applicators 10 can be custom-made applicators 10 that have significantly improved registration to a target area 11 as compared to one-size fits all applicators 10. Such applicators 10 can allow for smaller treatment areas 12 to be defined, as less tolerance for shifting or misalignment of the applicator 10 on the target area 11 needs to be accounted for in such custom-made applicators 10. Such custom-made three-dimensional applicators 10 can be any of those described in U.S. Patent Application Publication Nos. 2017/008566, 2017/0354805, and 2017/0354806, the respective disclosures of which are incorporated herein by reference.

The applicator 10 can be a two-dimensional structure, or a three-dimensional structure. The methods in accordance with embodiments of the disclosure can illustrate the improvement in registration of a treatment area 12 with a condition 13 to be treated on the target area 11

Throughout the discussion below reference will be made to the second set of data. It should be understood herein that similar steps, adjustments, manipulations, and uses of the data disclosed herein with reference to the second set of data can be applicable to the third set of data or fourth set of data or any set of data similarly associated with an applicator.

Figure 5:
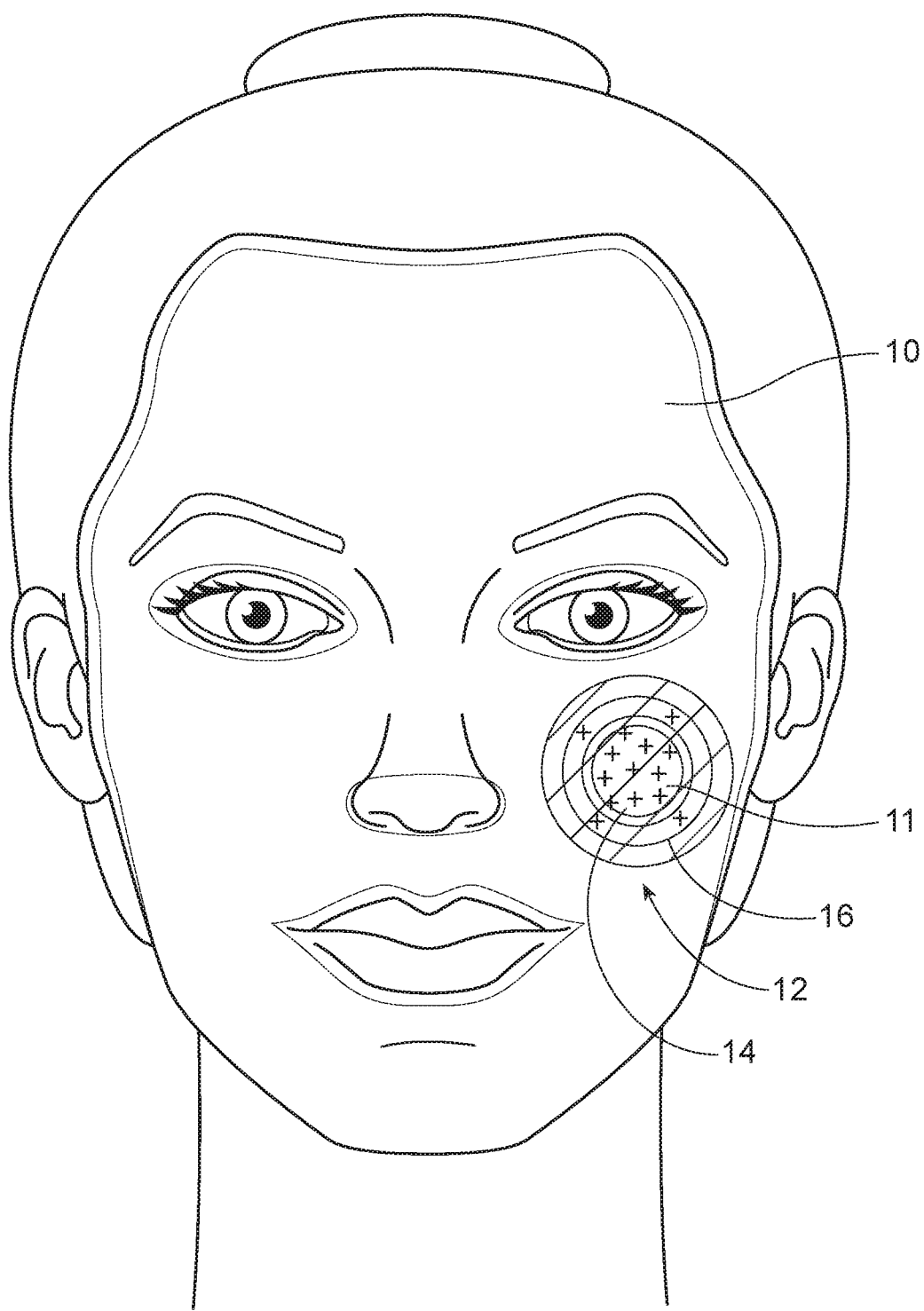
FIG. 5 is a schematic illustration of an overlay of an applicator on a target area showing the treatment area being defined over the condition in accordance with embodiments of the disclosure.

Referring to FIG. 1, a method of registering an active agent with a condition 13 to be treated by the active agent and/or defining a treatment area 12 on the applicator 10 can include receiving on a processor a first set of data representing the target area 11 and at least one condition 13 disposed on the target area 11 to be treated by the active agent. The method further includes receiving on a processor a second set of data representing at least a portion of an applicator 10 designed to contact the target area 11. The method can further include digitally overlying the second set of data over the first set of data to generate a first digital overlay. The method can also include digitally defining at least one treatment area 12 on the first digital overlay such that the at least one treatment area 12 surrounds the at least one condition. The method can also include generating a third set of data representing the at least a portion of the applicator 10 and the at least one treatment area. The method can include digitally overlaying the third set of data over the first set of data to generate a second digital overlay representing coverage of the at least one condition 13 by the at least one treatment area. Referring to FIG. 5, the method can also include generating a first electronic image that visually depicts the second digital overlay, showing the coverage of the at least one condition 13 by the at least one treatment area.

Figure 2:
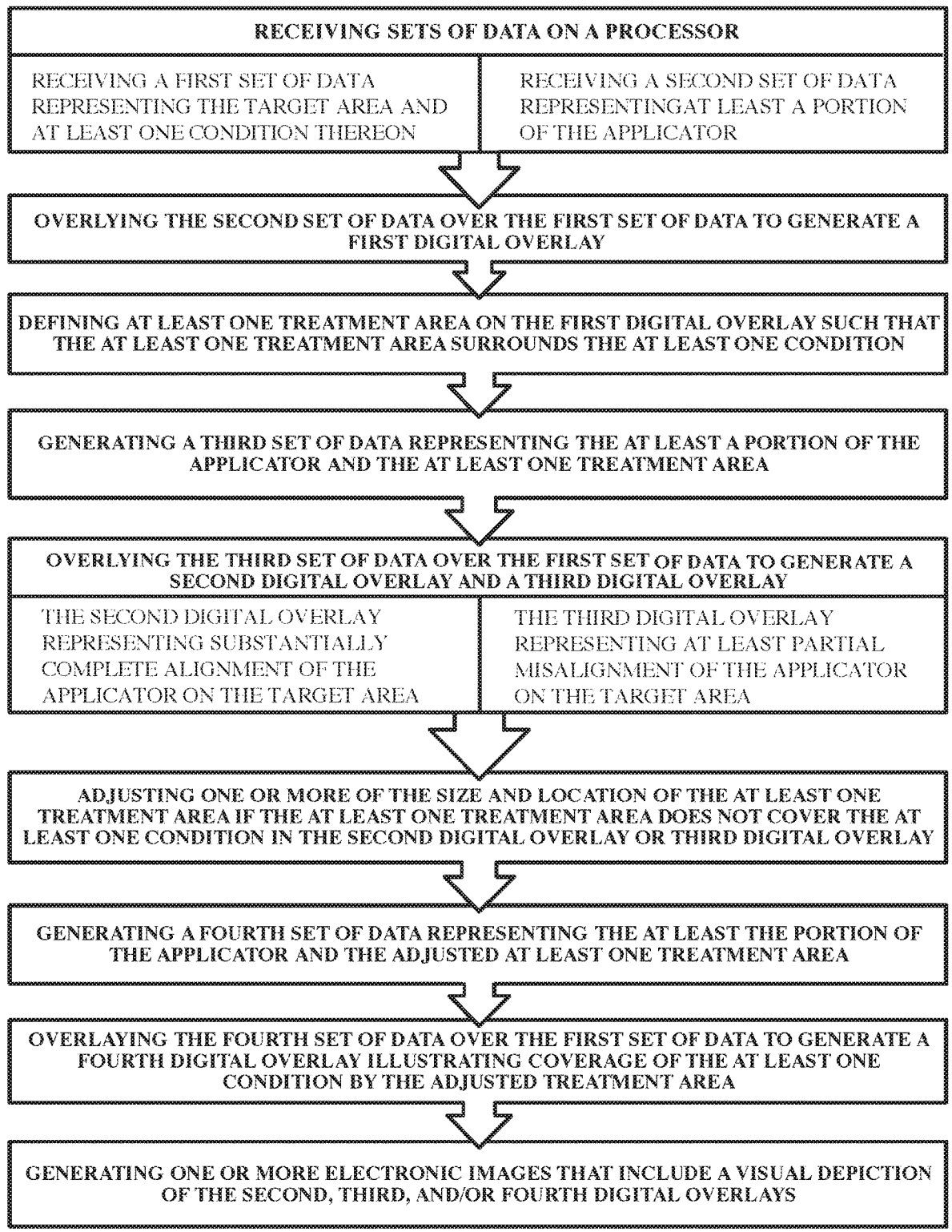
FIG. 2 is a process diagram illustrating a method in accordance with embodiments of the disclosure.

Referring to FIG. 2, the method can include definition of the treatment area 12 to accommodate misalignment of the applicator 10 when applied. In such embodiments, the method can include receiving on a processor a first set of data representing the target area 11 and at least one condition 13 disposed on the target area 11 to be treated by the active agent. The method can further include receiving on a processor a second set of data representing at least a portion of an applicator 10 designed to contact the target area 11. The method can further include digitally overlying the second set of data over the first set of data to generate a first digital overlay. The method can also include digitally defining at least one treatment area 12 on the first digital overlay such that the at least one treatment area 12 surrounds the at least one condition. The method can also include generating a third set of data representing the at least a portion of the applicator 10 and the at least one treatment area. The method also includes digitally overlaying the third set of data over the first set of data to generate a second digital overlay. In the second digital overlay, the applicator 10 can be digitally aligned with the target area 11 to have perfect or near perfect alignment between the target area 11 and the applicator. The method can further include digitally overlaying the third set of data over the first set of data to generate a third digital overlay representing at least some misalignment between the applicator 10 and the target area 11. For example, for a custom 3D mask, the target chemistry can be delivered to the target location on the target surface with good accuracy, hitting the target within a 2 mm+/−1 mm average offset whereas with a 2D substrate mask applicator, the offset can be as much as 6 mm on average+/−3 mm. So, misalignments can be quite large.

The treatment area on the applicator can totally or substantially cover the target area, the treatment area on the applicator can cover 99% or the target area, 95%, 90%, 80%, 75%.

The user can select regions of interest for treatment or they can be selected automatically. The strength of actives (thickness, amount, or percentage of active ingredient) can also be changed per region automatically or selected by the user. Nordson picojet systems, for example, can be used to deposit chemistry in lines or dots onto a 2D or 3D surface. The digital overlaying of the third set of data and the first set of data can be repeated with various misalignments of the applicator 10 and the target area 11. The misalignments can be different in the degree of misalignment and/or the direction of misalignment. This can be beneficial in capturing misalignments that can occur when an applicator 10 is actually applied to a target area 11 by a user.

Where multiple overlays are generated to represent misalignment of the applicator 10 and the target area 11, the at least one treatment area 12 can be analyzed in each overlay and adjusted if needed to maintain coverage of the condition. For example, the size and/or location of the at least one treatment area 12 can be adjusted if needed to accommodate a misalignment. The method can then further include generate a fourth set of data representing the at least the portion of the applicator 10 and the adjusted at least one treatment area. This fourth set of data can be digitally overlaid with the first set of data to generate a fourth digital overlay. While reference is made herein to a fourth digital overlay, it should be understood that numbering of the overlay could be different if multiple misalignment overlays are generated by overlay of the third set of data with the first set of data.

The method can further include generating one or more electronic images that each includes a visual depiction of any one or more of the digital overlays. For example, the method can include generating an electronic image of second digital overlay (showing alignment), third digital overlay (showing misalignment), and fourth digital overlay (showing the adjusted treatment area) to illustrate how the treatment area 12 was effectively adjusted to allow for coverage of the condition 13 despite misalignment. An electronic image of only the final digital overlay showing the final applicator 10 and defined treatment area 12 overlaid over the target area 11 and condition. Any number of electronic images and comparisons there-between can be generated in embodiments of the disclosure. Any known methods or software for generating an electronic image providing a visual depiction can be used.

The method can include generating a visual depiction comparing the first electronic image to the second or third (and/or any subsequent) electronic image. For example, the visual depiction can be a side-by-side view of the first and second electronic images. The method can include displaying the first electronic image before the second electronic image. The method can include displaying the second electronic image before the first electronic image. Any know methods or software for generating a visual depiction of one or more sets of data or electronic images can be used.

Any number of conditions 13 and associated treatment areas 12 can be present. A condition 13 can be divided into two or more treatment areas 12. Two or more conditions 13 can be combined to be covered by a singed defined treatment area. The target area 11 can include conditions 13 that are dispersed in isolated regions across the target area 11 and/or conditions 13 that are adjacent other conditions 13. One or more active agents can be used for treating various conditions 13. The method can include defining a treatment area 12 for each condition 13 in the treatment area.

Figure 4:
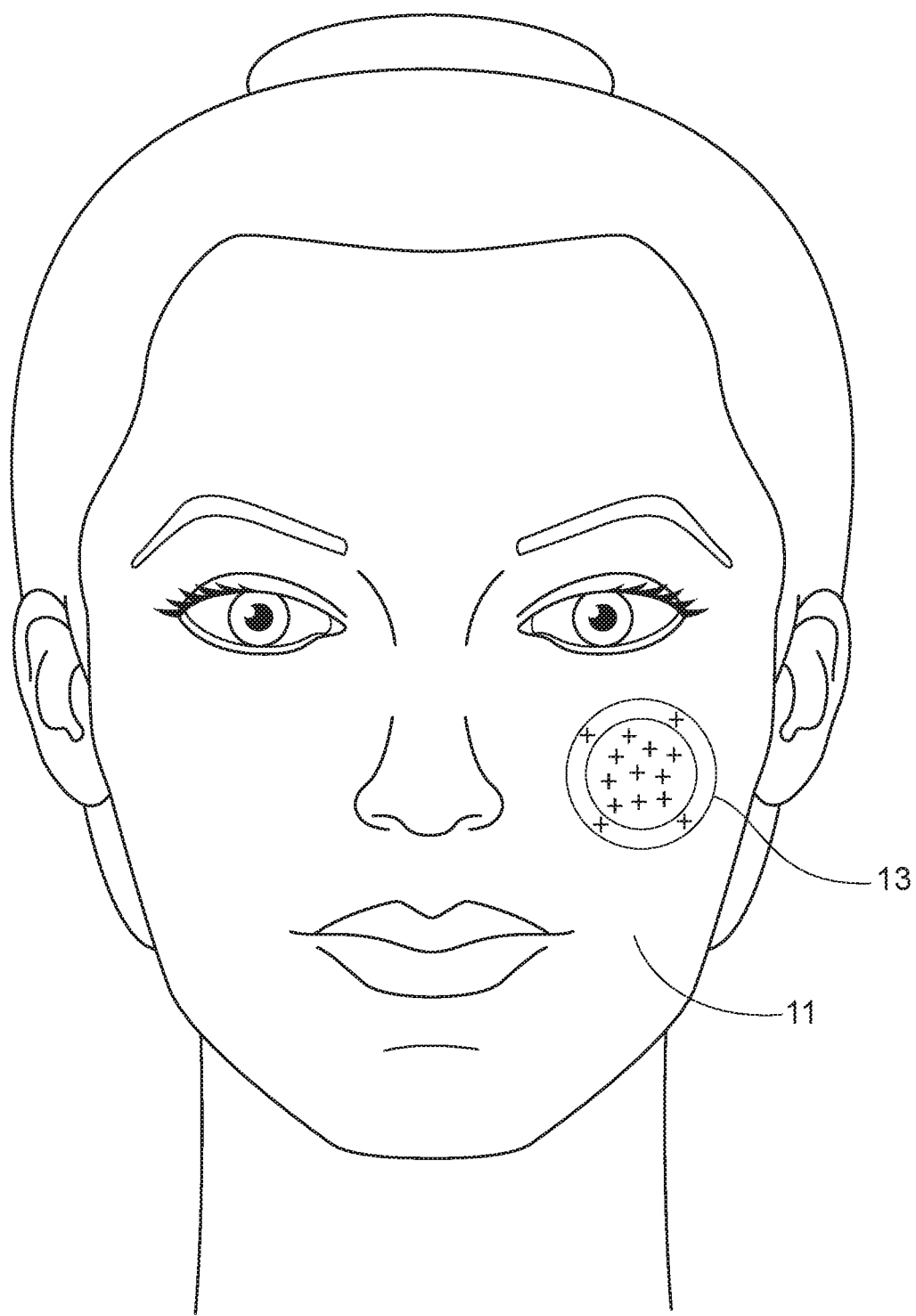
FIG. 4 is a schematic illustration of a digital geometric representation of a target area having a condition, with an intensity of the condition being illustrated.

Referring to FIG. 4, in embodiments, the treatment area 12 for an associated condition 13 can be divided into one or more zones for defining a concentration gradient of the active within a treatment area 12 or with a zone immediately adjacent to the treatment area 12 and/or provide a blending region between two treatment areas 12. The gradient concentration can mirror an intensity profile of the skin condition 13 within a treatment area. For example, a first zone 14 can be defined at a point or region of highest intensity of the condition 13 and a second zone 16 can be defined a point or region of lowest intensity of the condition 13 and a gradient concentration of the active agent can be defined between the first and second zones 14, 16. The third set of data can include information regarding the zones, if present. In embodiments, the electronic image can provide a visual depiction that includes illustration of the concentration gradient in the treatment area.

The digital geometric representation of the target area 11, and/or an applicator 10 can be streamed in real time, received from a memory, or received direct from the capture source, such as a three-dimensional scanner. The digital geometric representation of the target area 11 or the applicator 10 can be obtained using one or more of three-dimensional scanners, two-dimensional scanners, cameras, smartphone camera, digital applications for tablets and phones, and other known equipment for obtaining digital geometric data. An Artec Spider, available from Artec Group Palo Alto, Calif. is an example of a suitable three-dimensional scanner. An example mobile application for a cellular phone or table is 123D Catch from Autodesk or Bellus3D from Bellus3D.

Figure 3:
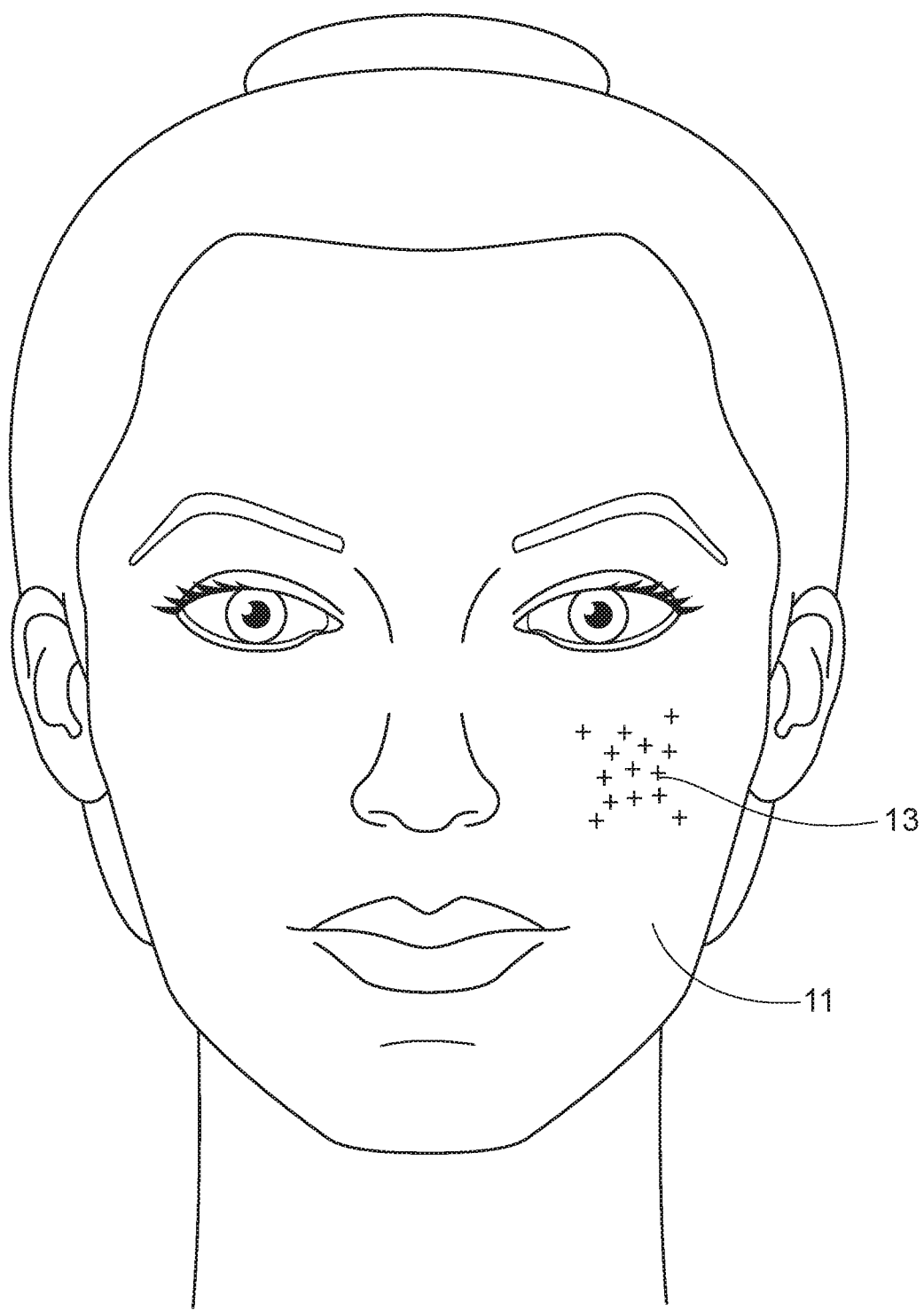
FIG. 3 is a schematic illustration of a condition on a target area, the target area being a human face.

Referring to FIG. 3, the first set of data can be received from a digital geometric representation of the target area 11 stored on a memory or streamed in real time. The digital geometric representation can include further information regarding the target area 11, such as coloring, texture, and other relevant information regarding the target area 11 and the condition 13 contained therein. For example, the first set of data can include information regarding intensity of the condition. Such information can be obtained through fluorescence imaging, heat imaging, Visia scanners, Vectra scanners or any instruments that use various types of light, polarized light, certain wavelengths of electromagnetic radiation to measure or diagnose skin condition. The first set of data can be modified to include information regarding the condition 13 which may not be captured by the digital geometric representation.

The digital geometric representation of the target area 11 or the applicator 10 can be used as a whole or partitioned with only a portion of the total representation being used. Furthermore, portions of the geometry derived from the scan or other imaging technique can be removed or edited from the digital geometric representation. The digital geometric representation data may be used without alteration, or the geometry of the representation may be altered. For example, digital processing (e.g. smoothing, gap filling, interpolation, down sampling, etc.) may be used to alter the digital data. For example, the digital data can be altered to be provided as a mesh to allow for measurement of various features on the digital data. For example, a two-dimensional set of data from an image or scan can be altered to provide a three-dimension representation of the two-dimensional data.

Any one or more of the various digital processing equipment, digital geometric representations, graphics programs, and graphical displays may be stored in a tangible computer readable memory or medium and/or shared or cloud-based medium, and execute one or more processors to perform the functions described herein. For example, the digital geometric representation can be obtained by a user using a smartphone camera and/or mobile application and subsequently uploaded to a manufacturer's shared memory or medium for manufacturing of the mask. Alternatively, digital geometric representations can be obtained with scanners or other imaging devices located at the point of sale of the mask. The data from the digital geometric representations can be stored locally or on a shared medium.

The digital geometric representation of the target area 11 or the applicator 10 can be stored on a memory or shared medium and transmitted to a processor. the digital geometric representation of the target area 11 or the applicator 10 can be stored on a memory of the scanning or capture device and transmitted by the device or other means to a processor. For example, the scanning or capture device can store the digital geometric representation in whole or in part, including, on a buffer memory for transmitting the digital geometric representation to the processor in buffering mode.

The target area 11 can be a human face or portion thereof and the applicator 10 can be a mask for covering the face or portion thereof. The target area could be another part of the body such as, arms, elbow, knee, wrist, hands, fingers, neck, or other body part. The mask can include or have applied thereto one or more cosmetic, therapeutic, and active agents for treating the face or skin or skin conditions 13 thereon. The mask can be a two-dimensional mask (e.g. sheet mask, substrate, nonwoven, woven, knit, gel, film, foil or hydrogel mask or any other material) or a three-dimensional mask made of any material. In any of the embodiments disclosed herein, the three-dimensional mask can be a self-supporting mask. As used herein, the term "self-supporting" means that an element of or the applicator 10 in its entirety retains a substantial portion of a defined three-dimensional shape without the aid of external support structures when resting on a horizontal surface in air. The mask can be a single-dose applicator 10 or for single use having a single-dose of the active, cosmetic, and/or therapeutic. As used herein, the term single-dose means an applicator 10 comprising sufficient active agents to afford a user only a single application of the active agent via the applicator. The mask can be for multiple use. For example, active, cosmetic, and/or therapeutic agents can be applied and successively reapplied for multi-use. There may be indicia present on the mask to indicate the location of the active agent or indicia to help with reapplication of active agent to the application for the case of a durable reusable applicator. The indicia may be any combination of colors, text, lines, illustrations, texture, or other forms of indicia. In any of the embodiments disclosed herein, the mask can be disposable. As used herein, the term disposable refers to applicators 10 intended to be discarded after use rather than durable, or semi-durable implements intended for multiple users either with or without the reapplication of an active agent. The mask can be a durable item suitable for washing by hand or in a dishwasher or clothing washing machine.

The target area 11 is a human face. The digital representation of the human face can be constrained in space from the backside to represent the bone internal to the skull. For example, in embodiments, the inner surface of the digital representation, corresponding to the underlying bone is treated as a rigid surface and constrained in space. The nodes on the inner surface of the skin are thus fixed in place and not allowed to move. This can be accomplished in known finite element simulation packages, for example, as a boundary condition.

The digital representation can be further modified to have mechanical properties simulating that of the target area 11. For example, when the target area 11 is a human face the digital representation or resulting mesh can be given a thickness representing the skin surface. For example, the thickness can be about 0.5 mm to about 4 mm, about 1 mm to about 3 mm, or about 2 mm to about 4 mm. Other suitable thickness can be about 0.5, 1, 2, 3, or 4, mm. In embodiments, the thickness can be constant. The thickness can vary according to different regions of the target area 11 or entire face. The digital representation or set of data resulting from the digital representation can be given material surface properties as, well. For example, where the target area 11 is the human face, the digital representation or digital data can be given properties to simulate the mechanical properties of the dermis and epidermis layers. For example, a stiffness model can be used to simulate the mechanical properties for the epidermis and dermis as a single bulk layer. The model can include specification of one or more properties including for example, the stiffness, Poisson ratio, and viscoelastic behaviors. Alternately, the mechanical properties of the dermis and epidermis layers can be simulated as two separate layers.

The second set of data represents the applicator. The second set of data can be manipulated, for example, from a digital representation to a mesh. The second set of data can be further manipulated to include mechanical properties of the material of the applicator. For example, the applicator 10 can be rigid and such rigidity can be simulated in the second set of data. The applicator 10 can be flexible. Where the second set of data represents a two-dimensional mask, mechanical properties of a wet cotton substrate SKII FTE mask can be used, for example.

In yet other embodiments, the applicator 10 can be a self-supporting structure and such resilient nature of the applicator 10 under applied force can be similarly simulated in the second set of data. The applicator 10 can have an active, therapeutic, cosmetic or other agent applied thereto. The adhesive nature of such ingredients on a mask can be incorporated into the second set of data to simulate the self-adherent property of an applicator 10 on a target surface. The second set of data can be manipulated to simulate a wet applicator 10 or a dry applicator.

The mask or applicator 10 can include any suitable active, cosmetic, or therapeutic agent to be applied to the face of the user. For example, active, therapeutic, and/or cosmetic agents can include active ingredients, carriers, chassis, emulsions, hydrogels, adhesives, process aides (such as thickeners, rheology modifiers, etc.). Active agents may further comprise a release layer to help active agents transfer from the applicator 10 to the target surface. Active agents may include adhesive materials, active chemical agents, absorbent materials such as absorbent gel materials or absorbent foam materials placed according to either the diagnostic scan or relative to identifiable features. As an example, it may be desirable to dispose an absorbent foam material along cheekbones, brow or nose of a scanned user's facial mask, the disposition sites may be determined according to the geometry of the representation rather than according to the diagnostic scan of the user. Active agents may be in one or more physical forms, including but not limited to: foams, liquids, powders, films, fibers, creams, gels, hydrogels, encapsulated active agents, solids, combinations of these forms and other forms. Some examples of active agents include but are not limited to: moisturizer, anti-aging, anti-wrinkle, skin tone control, anti-irritation, sensates (e.g. menthol), heating or cooling chemistries, skin tightening, hair removal, hair regrowth, fungicide, antibacterial, antiviral, surfactants, cleaning agents, copper ion eluting (such as from Cupron of Richmond, Va.), antioxidants, vitamins, sunscreen, rejuvenation agents, wound healing agents, sebum management agents, astringents, exfoliates, anti-inflammatory, leave on, overnight, dry skin, itchy skin, cracked skin, peptides, acne, scar treatments, sore muscles treatments, medicaments including pharmacological actives to treat disease states or other acute or chronic issues such as eczema, rashes, acne, cancer, cold sore, Psoriasis, Rosacea, Vitiligo, warts, Herpes, fungal infection, Actinic Keratosis, ulcers, shingles, poison ivy, and insect bites. Further, the medicaments, including pharmacological actives, can go beyond topical effect and be designed for transdermal delivery of an active into the bloodstream or other internal tissue. Examples of therapies, both prescribed and un-prescribed include: nicotine, Botox, and hormone supplements.

Exemplary active agents for cosmetic changes to the target structure include: hydrating agents, acne treating agent, anti-aging agents, ant-wrinkle agents, matte-finish compounds, under-eye hydrating agents, anti-oil agents, primer, lipstick, lip gloss, lip liner, lip plumper, lip balm, lip conditioner, lip primer, lip boosters, concealer, foundation, powder, rouge, blush, blusher, contour powder/creams, highlight, bronzer, mascara, eyeliner, and setting materials, scents, perfume or fragrance compositions (e.g. essential oils).

The inclusion of one or more scents, perfume or fragrance compositions may be applied to the mask for subsequent deposition to the face. However, a portion, or all, of the included one or more scents, perfume or fragrance compositions may act as experience agents. The experience agent provides a smell in the environs of the mask when in use. For example, the smell provided by a fragrance to suggest outdoor flower garden aroma may be desirable when applying cosmetic agents to the face of a consumer/wearer. Experiential agents need not necessarily be located on the target structure contact surface of the mask. The agents may be located in a region not in contact with the target structure, such as on a non-contacting portion of the application side of the applicator 10 or anywhere on any applicator 10 side that is non-contacting to the target structure. The experience agent may be selected to accompany a selected appearance feature. In one embodiment, the indicia may comprise the active agent deposited upon the first structural element without alterations to the relative color or texture of the application site.

Any of the foregoing properties or materials can be simulated in the second set of data where such materials or ingredients may affect the mechanical properties of the applicator, the positioning and/or retention of the applicator 10 on the target surface.

The overlaying of the data representing the applicator 10 and the data representing the target area 11 can include converting the first set of data to a first mesh and converting the second set of data corresponding to the applicator 10 to a second mesh and aligning the two meshes using software such as, but not limited to, Artec Studio 12 Professional (Artec Software). Any of the disclosure herein is similarly applicable to the overlying of the third and first sets of data or any other set of data associated with an applicator 10 and target area 11. The meshes can be imported into the software in any suitable file format, including, for example, STL, OBJ, PLY, and other 3D mesh file formats. Once imported, the first mesh and the second mesh are manually brought into rough alignment. The first mesh, corresponding to the target surface, can be designated as fixed or registered and the second mesh can be designated as unregistered, thereby allowing the second mesh to be moved relative to the first mesh. Once roughly aligned, an align feature of the software can be used to bring the first and second meshes into refined alignment. Once aligned, both meshes can be selected and a measurement feature of the software can be used to calculate a distance between the two meshes at one or more points. For example, a surface-distance map calculation can be used. In embodiments, the search distance can be selected to be up to 10 mm, which represents the maximum distance between points in space the program will search for calculating separation distance. If a gap is greater than the search distance, that gap will not be included in the calculation. Any suitable search distance can be used. Once calculated, an electronic image illustrating the calculated distances graphically can be displayed.

The first and second set of data can be overlaid to simulate application of the applicator 10 to the target surface. Any of the disclosure herein is similarly applicable to the overlying of the third and first sets of data or fourth and first sets of data or any other sets of data representing the applicator 10 to overlay onto the first set of data. For example, the second set of data corresponding to the applicator 10 can be positioned a distance from the first set of data and a digitally applied force can be used to push the second set of data against the first set of data, thereby simulating application of the applicator 10 to the target area 11. For example, the applied force can be a distributed force on the applicator 10 or can be a localized force on the applicator. For example, in embodiments an initial load can be provided as localized points of force, can be applied to push the second set of data to the first set of data, simulating application of the applicator 10 and positioning of the user's fingers on the applicator 10 applying the localized load to position the applicator 10 onto the target area 11. Optionally, a distributed force can be applied to the second set of data after it is pushed against the first set of data, simulating a user applying further force across the applicator 10 to better adhere or smooth the applicator 10 to the target area 11. The adhesive force can also be used or incorporated into the force simulation for application and retention of applicator 10 on the target surface. For example, wet applicators 10 can include agents such as lotions, therapeutic agents, and other cosmetic agents that provide adhesive force. Additionally, or alternatively, wet applicators 10 can include a water component or have water added thereto to make the applicator 10 adhere to the target area 11. In embodiments, adhesive force of an applicator 10 can be assessed using a peel test, in which the force required to peel the wet applicator 10 away from the target area 11 is measured, and provides the resulting adhesive force per unit area. Such force can be incorporated into the set of data representing the applicator 10 to incorporate the adhesive force as an element to the simulation of the applicator 10 being applied to and retained on the target area 11. Any suitable applications of force and associated loads can be used and will vary depending on the target area 11 and type of applicator 10 being applied to the target area 11. Suitable force profiles and loads can be readily determined by the skilled person based on typical application of the applicator 10 or measured by actual application of an applicator.

The applicator 10 can be a two-dimensional applicator. In such embodiments, a finite element analysis can be used to bring the flat applicator 10 surface into contact with a three-dimensional target area 11 before application of the load.

The method can include a further step of removing the load after the second set of data is pushed into contact with the first set of data. The load can be removed for example, when a force balance is detected and steady state of force is achieved. The overlaid data can be manipulated in embodiments to include a representation of the cohesive force of the applicator 10 resulting, for example, from the ingredients applied to the inner surface of the applicator.

A static load or dynamic load can be used. Application of a dynamic load can be applied to allow the data sets to move relative to each other. In embodiments, steady state can be detected by a balance of force, and representing the point at which the objects stop moving relative to each other. The load can then be removed. In embodiments, the data sets representing the applicator 10 and the target area 11 can again be allowed to move relative to each other until motion ceases. For example, this can simulate any compression of the skin layer and then subsequent relaxation and motion after force is removed.

Once the overlaid model reaches a converged solution the at least one treatment area 12 can be defined or adjusted by defining a perimeter of the target area 11 and defining an expanded perimeter that surrounds the target area 11 perimeter and is spaced outwardly a distance from at least one point perpendicular from the treatment area perimeter. The expanded perimeter defining the at least one treatment area 12 is spaced outwardly perpendicular from all points of the perimeter of the target area 11. The expanded perimeter is spaced outwardly perpendicular from at least one point of the target area 11 perimeter by about 2 mm.

As discussed above, the overlaid model can be programmed to reach a converged solution having a misalignment between the set of data representing the applicator 10 and the set of data representing the target area 11 to simulate actual misalignment that can occur when the applicator 10 is applied by the user. In general, misalignment can be most significant for two-dimensional applicators where a user seeks to first align the eye holes and other portions may be out of alignment due to rotational offsets or lateral offsets. Another source of misalignment comes from two dimensional substrates deforming onto a three-dimensional target surface, which will inherently not match with perfect alignment the curvature of the three-dimensional target area. Such misalignment can be incorporated into the model when overlying a two-dimensional substrate over the first set of data representing the target area 11.

Misalignment can be accommodated by expanding the size of the at least one treatment area. For example, in embodiments, the outward spacing between the target area 11 perimeter and the expanded perimeter defining the at least one treatment area 12 can be selected to accommodate a misalignment, ensuring that even if misaligned the target area 11 will be contacted by the at least one treatment area. For example, the size of the treatment area can be expanded in one or more directions or can be expanded in all directions from the perimeter of the target area 11.

Figure 6:
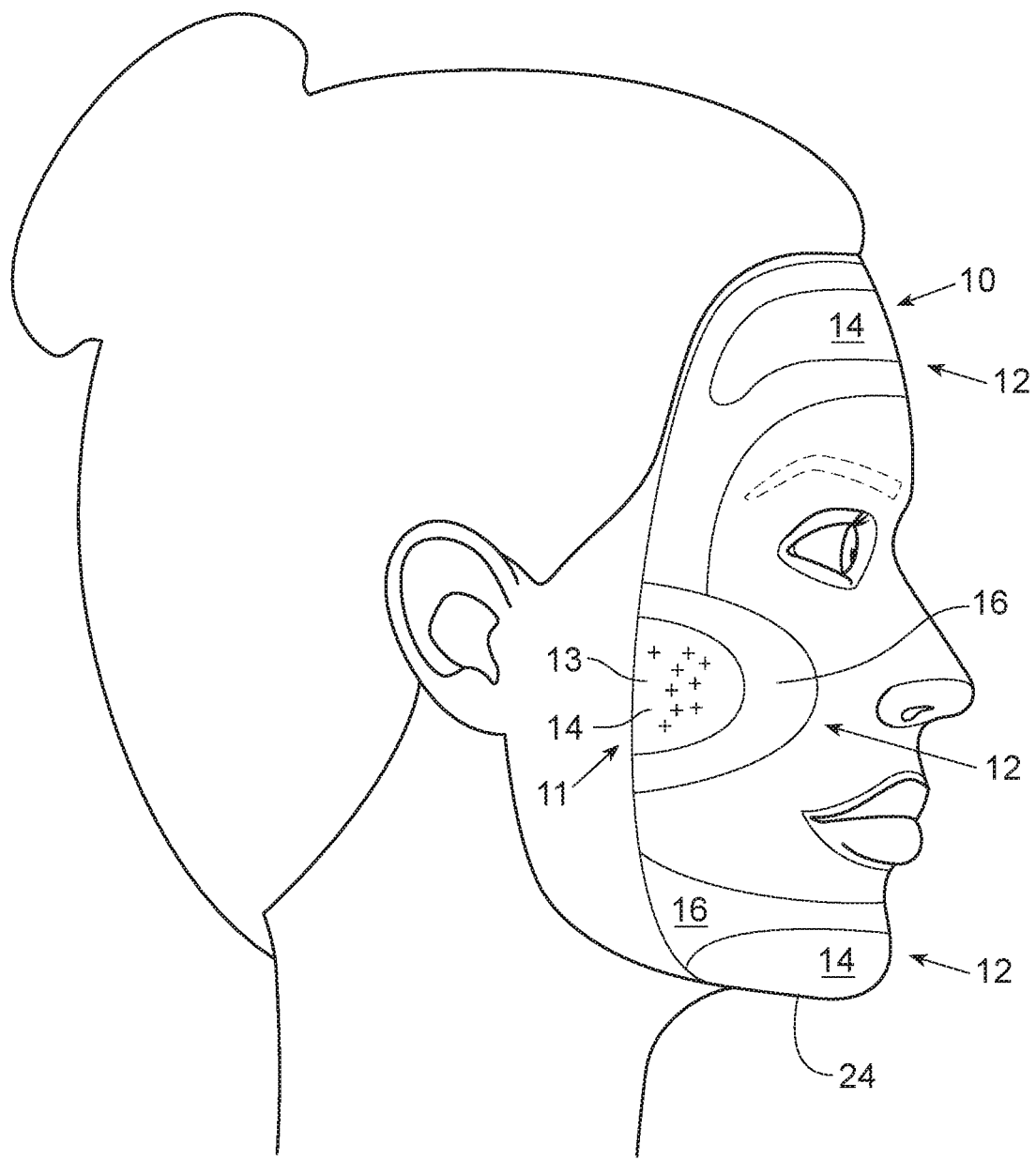
FIG. 6 is a schematic illustration of an applicator having a gradient concentration of active agent fitted to a face in accordance with embodiments of the disclosure.

Expanded treatment areas 12 can include a gradient application of the active agent in the treatment area. Referring to FIG. 6, for example, the method can include defining in the at least one treatment area a first zone 14 corresponding to the target area 11 and a second zone 16 corresponding to an enlarged portion of the treatment area 12 for accommodating misalignment. In embodiments, a decreasing concentration gradient can be provided form the first zone 14 to the second zone 16. This can be beneficial to ensure that there is some active in regions to contact the target area in the event of misalignment but a reduced amount of exposure to active for regions outside the target area if there is less than anticipated or no misalignment.

The at least one treatment area 12 can accommodate misalignment without expansion of the treatment area 12. For example, the at least one treatment area can be defined corresponding to the target area as discussed above and the misalignment can be accommodated by providing a gradient concentration of active agent decreasing from within the at least one treatment area to a peripheral zone surrounding the at least one treatment area.

The at least one treatment area 12 can include a concentration gradient within the treatment area. In embodiments, one or more actives can be provided in a gradient concentration between adjacent treatment areas 12. For example, target areas 11 can be adjacent another target area 11 or can be separated from target areas 11 in an isolated region of the applicator 10. Concentration gradients of active agents can be beneficial for various active agents, for example, allowing for controlled reduction of the concentration of an active agent at the periphery of the target area 11. Concentration gradients of the active can also be beneficial in avoiding abrupt changes in the presence of the active agent. For example, in many conventional applicators, the active is provided in the target area 11 as a patch and is sized to be the same or slightly larger than the target area 11. Immediately outside this sizing there is an abrupt change in that the active agent is not present. With some active agents, for example, skin lighteners, self-tanners, and the like, this can lead to an undesirable or unnatural effect on the target surface, such as a color difference in the surface that defined by a distinct line rather than a natural blend.

A gradient change to avoid such abrupt changes in the concentration of active and associated results on the target surface can also be beneficial when the target area 11 has or is adjacent to a curvature 24. The concentration gradient can be provided between a first zone 14 and a second zone 16 with a curvature or edge 24 zone disposed between the first and second zones or within one of the zones. FIG. 6 also illustrates an applicator having a zone crossing over a curvature 24 of the target surface in the chin region. The concentration gradient of the active can be a decreasing gradient from the first zone 14 through the curvature or edge 24 zone to the second zone. The concentration gradient 18 of the active can be a decreasing gradient from the first zone 14 to the curvature or edge 24 zone, and then increasing from the curvature or edge 24 zone to the second zone. The curvature or edge 24 can be in better contact with the applicator than surrounding more planar areas. For example, a gap or bubble in the applicator can result in the surrounding areas. Reduction of the concentration of the active agent in the curvature or edge 24 zone can aid in reducing or avoiding overexposure of the curved area or edge 24 to the active, which can result from the way in which the applicator contacts the surface in this target area 11.

Applicators having actives providing in a gradient can also be advantageous when applying to a target surface that benefits from different amounts of active agent. For example, an applicator for such a target surface can have a first zone 14 in which a high concentration of active agent is beneficial and a second zone 16 in which a lower concentration of active agent is beneficial. For example, the applicator can have a first zone 14 corresponding to the target area 11 and a second zone 16 corresponding to a periphery surrounding or a region adjacent to the target area 11. The target area 11 can be a peripheral area of a central zone, such that an increasing gradient concentration is provided from the central zone to the outer peripheral target area 11. The peripheral area can be the first zone 14 and a central zone can be the second zone 16. The active agent can be applied to the applicator in a concentration gradient decreasing from the first zone 14 to the second zone 16. Any number of zones can be provided for a given target area depending on the target area and the treatment to be applied.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of defining at least one treatment area of an applicator containing an active agent for treating a condition on a target area, comprising:
   receiving on a processor a first set of data representing the target area and at least one condition disposed on the target area to be treated by the active agent, the first set of data being received from a digital geometric representation of the target area stored on a memory or streamed in real time;
   receiving on a processor a second set of data representing at least a portion of an applicator designed to contact the target area;
   digitally overlying the second set of data over the first set of data to generate a first digital overlay;
   digitally defining the at least one treatment area on the first digital overlay such that the at least one treatment area surrounds the at least one condition;
   generating a third set of data representing the at least the portion of the applicator and the at least one treatment area;
   digitally overlying the third set of data over the first set of data to generate a second digital overlay representing coverage of at least one condition by the at least one treatment area; and
   generating a first electronic image that includes a visual depiction of the second digital overlay,
   wherein the first set of data further comprises data representing the intensity of the condition, wherein the condition is present with varying intensity, the method further comprising digitally defining within the treatment area a first zone corresponding to a region of the condition with the highest intensity and a second zone corresponding to a region with the lowest intensity, wherein the active agent is to be provided in a gradient of intensity corresponding to the intensity of the condition.

2. A method of defining at least one treatment area of an applicator containing an active agent for treating a condition on a target area, comprising:
   receiving on a processor a first set of data representing the target area and at least one condition disposed on the target area to be treated by the active agent, the first set of data being received from a digital geometric representation of the target area stored on a memory or streamed in real time;
   receiving on a processor a second set of data representing at least a portion of an applicator designed to contact the target area;
   digitally overlying the second set of data over the first set of data to generate a first digital overlay;
   digitally defining the at least one treatment area on the first digital overlay such that the at least one treatment area surrounds the at least one condition;
   generating a third set of data representing the at least the portion of the applicator and the at least one treatment area;
   digitally overlying the third set of data over the first set of data to generate a second digital overlay representing coverage of at least one condition by the at least one treatment area; and
   generating a first electronic image that includes a visual depiction of the second digital overlay, wherein digitally defining the at least one treatment area comprises measuring on the first digital overlay a maximum height and maximum width of the at least one condition and defining the at least one treatment area to have a height and width that is at least equal to the height and width of the skin condition.

3. The method of claim 2, wherein the at least one treatment area is defined to have a height and/or width that is at least 10% to 50% larger than the measured height and width of the at least one condition.

4. A method of defining at least one treatment area of an applicator containing an active agent for treating a condition on a target area, comprising:
   receiving on a processor a first set of data representing the target area and at least one condition disposed on the target area to be treated by the active agent, the first set of data being received from a digital geometric representation of the target area stored on a memory or streamed in real time;
   receiving on a processor a second set of data representing at least a portion of an applicator designed to contact the target area;
   digitally overlying the second set of data over the first set of data to generate a first digital overlay;
   digitally defining the at least one treatment area on the first digital overlay such that the at least one treatment area surrounds the at least one condition;
   generating a third set of data representing the at least the portion of the applicator and the at least one treatment area;
   digitally overlying the third set of data over the first set of data to generate a second digital overlay representing coverage of at least one condition by the at least one treatment area; and
   generating a first electronic image that includes a visual depiction of the second digital overlay, wherein digitally defining the at least one treatment area comprises digitally tracing an outer bound of the at least one condition and defining the at least one treatment area to have an outer bound that is disposed at or outboard of the outer bound of the at least one condition, and wherein the outer bound of the treatment area is defined to be disposed at least 10% to 50% outboard of the outer bound of the at least one condition.

5. A method of defining at least one treatment area of an applicator containing an active agent for treating a condition on a target area, comprising:
   receiving on a processor a first set of data representing the target area and at least one condition disposed on the target area to be treated by the active agent, the first set of data being received from a digital geometric representation of the target area stored on a memory or streamed in real time;
   receiving on a processor a second set of data representing at least a portion of an applicator designed to contact the target area;
   digitally overlying the second set of data over the first set of data to generate a first digital overlay;
   digitally defining the at least one treatment area on the first digital overlay such that the at least one treatment area surrounds the at least one condition;
   generating a third set of data representing the at least the portion of the applicator and the at least one treatment area;

digitally overlying the third set of data over the first set of data to generate a second digital overlay representing complete alignment of the applicator on the target surface and illustrating coverage of the at least one condition by the at least one treatment area;

digitally overlaying the third set of data over the first set of data to generate a third digital overlay representing at least partial misalignment of the applicator on the target surface and illustrating coverage of the at least one condition by the at least one treatment area;

adjusting one or more of the size and or location of the at least one treatment area if at least one treatment area does not cover 99% or 75-95% of the at least one condition in the second digital overlay; and/or the at least one treatment area does not cover all of the at least one condition in the third digital overlay to create an adjusted treatment area;

generating a fourth set of data representing the at least the portion of the applicator and the adjusted treatment area;

digitally overlaying the fourth set of data over the first set of data to generate a fourth digital overlay representing complete alignment of the applicator and/or the at least partial misalignment of the applicator on the target surface and illustrating coverage of the at least one condition by the adjusted at least ono treatment area; and generating one or more of:
a first electronic image that includes a visual depiction of the second digital overlay,
a second electronic image that includes a visual depiction of the third digital overlay, and
a third electronic image that includes a visual depiction of the fourth digital overlay.

6. The method of claim 5, comprising repeating the overlying of the third set of data over the first set of data one or more times with different at least partial misalignment of the applicator on the target surface and illustrating coverage of the at least one condition by the at least one treatment area with each one of the different at least partial misalignment of the applicator on the target surface.

7. The method of claim 5, further comprising creating an applicator having the active agent applied in the treatment area using the fourth set of data.

8. The method of claim 5, wherein the misalignment of the applicator on the target area is selected such there is 90% to 99% alignment between the applicator and the target area.

\* \* \* \* \*